US010058500B2

(12) United States Patent
Quidant et al.

(10) Patent No.: US 10,058,500 B2
(45) Date of Patent: Aug. 28, 2018

(54) METHOD FOR ENHANCED PHOTOEPILATION BASED ON METALLIC NANO-COMPLEXES

(75) Inventors: Romain Roger Quidant, Castelldefels (ES); Ignacio de Miguel Clave, Castelldefels (ES); Mark Kreuzer, Castelldefels (ES)

(73) Assignees: Fundació Institut de Ciències Fotòniques, Barcelona (ES); Institució Catalana de Recerca I Estudis Avançats, Barcelona (ES)

(*) Notice: Subject to any disclaimer, the term of this patent is extended or adjusted under 35 U.S.C. 154(b) by 942 days.

(21) Appl. No.: 14/361,629

(22) PCT Filed: Nov. 30, 2011

(86) PCT No.: PCT/EP2011/071386
§ 371 (c)(1),
(2), (4) Date: Jun. 30, 2014

(87) PCT Pub. No.: WO2013/079105
PCT Pub. Date: Jun. 6, 2013

(65) Prior Publication Data
US 2014/0316394 A1    Oct. 23, 2014

(51) Int. Cl.
*A61B 18/18* (2006.01)
*A61K 8/73* (2006.01)
(Continued)

(52) U.S. Cl.
CPC .............. *A61K 8/736* (2013.01); *A61B 18/18* (2013.01); *A61K 8/0245* (2013.01); *A61K 8/19* (2013.01);
(Continued)

(58) Field of Classification Search
CPC ........ A61B 18/203; A61B 2018/00452; A61B 2018/00476; A61N 5/06; A61N 5/0616;
(Continued)

(56) References Cited

U.S. PATENT DOCUMENTS 9,768,355 B2 * 9/2017 El-Shall ............ H01L 33/343
2005/0172852 A1 * 8/2005 Anderson .......... C09D 11/50
106/31.03
(Continued)

FOREIGN PATENT DOCUMENTS

WO   WO-01/26635 A2     4/2001
WO   WO-2006/122222 A2  11/2006
WO   WO-2012/027728 A2  3/2012

OTHER PUBLICATIONS

Lademann et al., "Triggered release of model drug from AuNP-doped BSA nanocarriers in hair follicles using IRA radiation," Acta Biomaterialia 30 (2016) 388-396.*
Cao et al. "Gold nanorod-based localized surface plasmon resonance biosensors: A review," Sensors and Actuators B 195 (2014) 332-351.*
(Continued)

*Primary Examiner* — Ahmed Farah
(74) *Attorney, Agent, or Firm* — Marshall, Gerstein & Borun LLP (57) ABSTRACT

The present invention relates to a composition for topical application on skin for photoepilation comprising nanocomplexes which comprise a nanoparticle supporting an LSP resonance which is coated with at least a chemical compound, wherein said chemical compound is selected from the group consisting of polyionic polymers, heterobifunctional compound of the surface assembled monolayer type, antibodies and their mixtures. The present invention also relates to a photoepilation method which comprises the steps of (i) applying to the skin surface the composition for topical application of the present invention, and (ii) applying a radiation to said surface of the skin.

24 Claims, 10 Drawing Sheets

(51) Int. Cl.
  *A61K 8/46* (2006.01)
  *A61Q 9/04* (2006.01)
  *A61K 8/81* (2006.01)
  *A61K 8/02* (2006.01)
  *A61K 8/19* (2006.01)
  *A61Q 9/00* (2006.01)

(52) U.S. Cl.
  CPC .............. *A61K 8/46* (2013.01); *A61K 8/8117* (2013.01); *A61Q 9/00* (2013.01); *A61Q 9/04* (2013.01); *A61B 2018/1807* (2013.01); *A61K 2800/413* (2013.01); *A61K 2800/624* (2013.01); *A61K 2800/81* (2013.01)

(58) Field of Classification Search
  CPC ........ A61N 5/0617; A61N 5/062; A61K 8/11; A61K 8/18; A61K 8/19; A61K 8/23; A61K 8/30; A61K 8/736; A61K 9/5084; A61K 9/51; A61K 9/0092; A61K 9/1075; A61K 9/1273
  USPC ....... 606/3, 9; 607/88–91, 96; 424/489, 490, 424/493, 479; 128/898
  See application file for complete search history.

(56) References Cited

U.S. PATENT DOCUMENTS

2005/0203495 A1* 9/2005 Malak .................. A61B 18/203
  606/9
2012/0265122 A1* 10/2012 El-Shall ............. A61K 41/0052
  604/20
2014/0105982 A1* 4/2014 Oldenburg ................ B22F 1/02
  424/489

OTHER PUBLICATIONS

Petryayeva et al., "Localized surface plasmon resonance: Nanostructures, bioassays and biosensing—A review," Analytica Chimica Acta 706 (2011) 8- 24.*
How is LSPR different from SPR, https://nicoyalife.com/technology/surface-plasmon-resonance/localized-surface-plasmon-resonance-theory/.*
International Search Report and Written Opinion issued in Application No. PCT/EP2011/071386 dated Sep. 9, 2012.
Huang et al., "Plamonic photothermal therapy (PPTT) using gold nanoparticles" *Lasers in Medical Science, Springer-Verlag, Lo,* vol. 23, No. 3, pp. 217-228 (Jul. 1, 2008).

* cited by examiner

NO DAMAGE

FIG. 8a

No damage

SEVERE DAMAGE

FIG. 10a

Severe damage

FIG. 10b

METHOD FOR ENHANCED PHOTOEPILATION BASED ON METALLIC NANO-COMPLEXES

FIELD OF THE INVENTION

The present invention relates to the cosmetic field and in particular to the field of photoepilation. More specifically, the invention relates to a composition for topical application in photoepilation. The composition consists of resonant nanocomplexes which are able to penetrate, upon application on the skin surface, into the hair follicle and stick to the hair cuticle. Once attached inside the hair follicle, they can be heated locally upon irradiation to damage the hair root and/or to slow the hair regeneration process. The invention also relates to a photoepilation method which comprises the steps of (i) applying said composition on the skin surface and (ii) applying a radiation to said surface of the skin. A very relevant advantage of this method relies in the uniform application to all hair types (dark or fair) with no dependence on the melanin content.

BACKGROUND OF THE INVENTION

Removal of unwanted hair is a common cosmetic concern. Traditional methods of hair removal which include shaving, waxing, tweezing, depilatory creams and electrolysis, result however only in temporary hair removal, can be painful and rely on techniques requiring multiple treatments.

Photoepilation (also known as light-based hair removal) is a non-surgical cosmetic method based on light technology to remove unwanted hairs and slow down or prevent their regeneration. The thermal effects generated during irradiation with a light source that can be either a laser or an intense pulsed light (IPL) are principally responsible for hair follicle alteration and damage. Thermal damage to the hair follicle is the consequence of light absorption by endogenous melanin. Results therefore are dependent on hair pigmentation, quantity of melanin present in the hair and the ratio between melanin concentration in the hair bulb and in the epidermis.

Since these approaches rely on the natural color (absorption) contrast between the hair and the skin, they consequently fail for fair hair (white, blond and auburn) and even in the ideal configuration of dark hair on pale skin the required light intensities are responsible for local skin injuries that can be long-lasting or even permanent. Methods have been developed to counteract these disadvantages, including the use of exogenous chromophores to increase the light absorption efficiency of the hair follicle in comparison with endogenous melanin absorption, and thus increase the safety of the procedure by reducing the laser power needed.

In this sense one of the recent approaches for hair removal is described in U.S. Pat. No. 6,287,549. Photosensitizers are encapsulated in a microsphere of size between 3-10 microns in diameter to obtain specific follicular targeting before laser irradiation. In general, these photosensitizers are exogenous chromophores and when used in conjunction with light renders them active. However, this approach presents among others the important drawback that the delivery of microspheres is non-specific, insofar as they do not only target the hair follicle, but can also be found in other skin areas such as the channels of sweat glands where they can cause damage and/or skin discoloration upon irradiation.

US2003/0059386 discloses topical compositions able to target hair follicles after initial hair removal from the follicles. Said compositions are able to selectively introduce photosensitizers or sonosensitizers compounds encapsulated in microparticles of size ranges between 1 to 70 microns. The composition is topically applied on skin, thereafter the compounds are released from the microparticles into the hair follicle and surrounding tissues, and then the skin is treated with electromagnetic or ultrasonic radiation. The compounds are thus activated, altering and/or killing cells responsible for hair growth. This hair removal method is however not completely satisfactory since microparticles reach surrounding tissues, and this causes upon irradiation, significant unwanted damage. Besides high radiation energies to activate compounds are needed which causes irritation and erythema.

Thus, in view of the above stated examples there remains the need in the state of the art to provide alternative and efficient photoepilation methods and compositions, which overcome all or at least part of the aforementioned drawbacks.

The solution provided by this invention is based on the fact that the inventors have discovered that resonant nanoparticles (NP) coated with at least a chemical compound applied on skin can be designed to target the hair follicle and attach to the hair cuticle via electrostatic interactions or to specifically bind to a target molecule present on the basal cells near the hair root. Once the coated resonant NP have attached to the hair, they can be locally and efficiently heated upon illumination due to their resonant properties, (with a reduced intensity/energy radiation) and destroy the hair without damaging surrounding tissues and/or glands. This approach presents the important advantage that the radiation needed for the present photoepilation method can then be of reduced intensity compared to conventional photoepilation methods.

BRIEF DESCRIPTION OF THE FIGURES

FIG. 6: *a*) and *b*) Two-photon luminescence microscopy images of hairs where nanocomplexes are shown to penetrate into the hair follicle (around 1 mm deep) demonstrating the attachment of chitosan nanocomplexes to the hair cuticle. *c*) Image of an untreated hair follicle as an autofluorescence reference.

FIG. 8: *a)* Schematic representation of a hair root with no damage

*b)* Bright field microscopy images of the hair root with no damage observed after Intense Pulsed Light (IPL) exposure.

FIG. 9: *a)* Schematic representation of the typical observable damage level to the hair root

*b)* Bright field microscopy images of the typical observable damage level observed after Intense Pulsed Light (IPL) exposure.

FIG. 10: *a)* Schematic representation of the typical observed severe damage level to the hair root

*b)* Bright field microscopy images of the typical observed severe damage level observed after Intense Pulsed Light (IPL) exposure.

DESCRIPTION OF THE INVENTION

In one aspect the present invention relates to a new composition for topical application in photoepilation comprising resonant nanocomplexes which are able to target and penetrate into the hair follicle after being applied to the skin and bind to the hair cuticle and/or the basal cells near the hair root where they accumulate. This new composition will be henceforth also referred to as the composition of the invention.

The nanocomplex present in the composition of the invention comprises a nanoparticle (NP) supporting a Localized Surface Plasmon (LSP) resonance which is coated with at least a chemical compound, said chemical compound being able to bond to the hair.

According to the present invention said chemical compound is selected from the group consisting of polyionic polymers, heterobifunctional compounds of the surface assembled monolayer type, antibodies and their mixtures.

The surface material of the NP according to the present invention is known to be a versatile surface that can be functionalised with various types of chemical compounds which are well known in the art. Thus, according to the present invention, the nanocomplexes of the composition of the invention can be readily obtained by well-known processes which comprise reacting a NP with at least one chemical compound as later defined. Said chemical compounds are able to coat the NP by forming at least a bond (coordinative or covalent) and in addition they enable, the resulting nanocomplex, to bind strongly to the hair.

Figure 1:
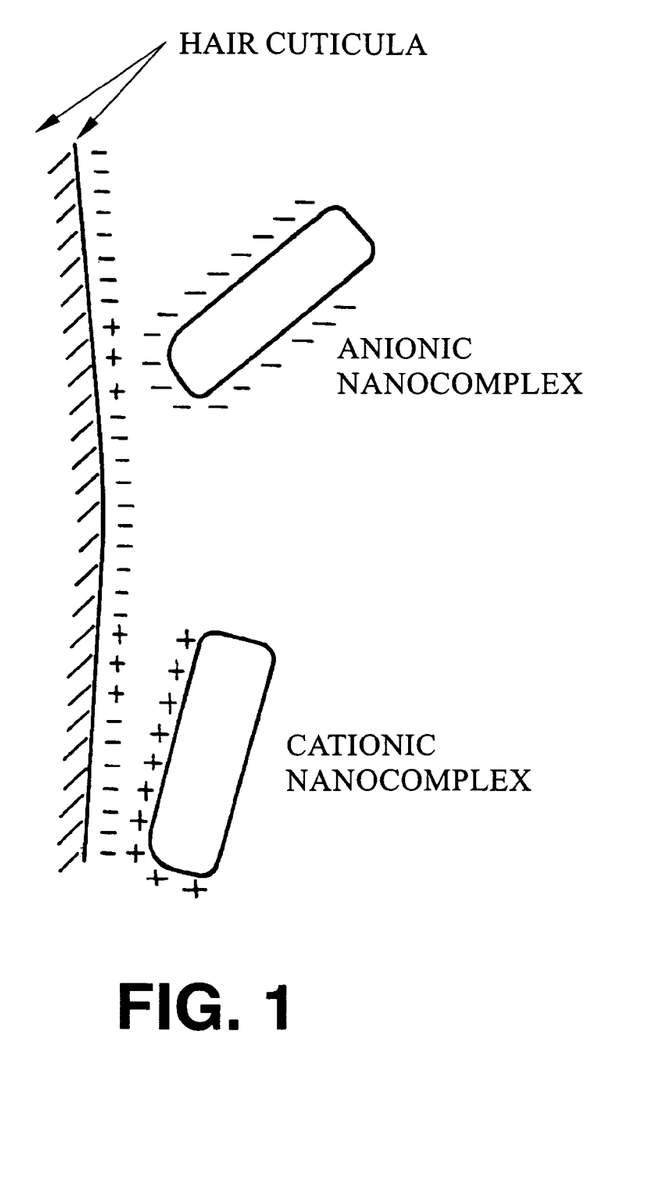
FIG. 1: Schematic illustration of the electrostatic interaction of anionic and cationic nanocomplexes with the hair cuticle.

According to a particular embodiment of the invention said chemical compound presents electrostatic affinity for the keratinized structures of the hair cuticle. In a particular embodiment this chemical compound is selected from the group consisting of polyionic polymers (both anionic and cationic) and their mixtures. In another particular embodiment said chemical compound is selected from the group of heterobifunctional compounds of the surface assembled monolayer type. Polyionic polymers and heterobifunctional surface assembled monolayers are able to strongly attach to the hair cuticle presenting a negatively charged keratinized part by electrostatic interactions. FIG. 1 schematically illustrates the case for the interaction of two differently coated nanocomplexes to the hair cuticle, a polianionic and a policationic nanocomplex.

According to another embodiment of the invention said chemical compound specifically binds through receptor-mediated processes, to a molecule target present on the basal cells of the hair, responsible for the hair growth, to cause maximal and irreversible damage to the hairs. Examples of said compounds in this case are antibodies, which can be easily obtained and thereafter chemically modified to be grafted to the NP surface according to well-known methods.

Many polyionic polymers have been described to interact with NP surfaces and be able to effectively cover it, transferring the intrinsic polymer property to the NP. Suitable polymers are polyanionic, polycationic and their mixtures.

In principle, nanocomplexes present in the composition of the invention can present any polyanionic polymer as coating, preferably cosmetically or pharmaceutically acceptable polymers. Preferred polyanionic polymers are selected from the group formed by biocompatible polycarboxylates, such as carboxymethyl cellulose and polyacrylates, and those conventionally used in hair care and conditioner products, such as polystyrene sulfonates, polyacrylic acid polymers (Carbopol®), and copolymers of vinyl acetate and crotonic acid. Polyanionic polymers with different molecular weights can also be used.

Figure 4:
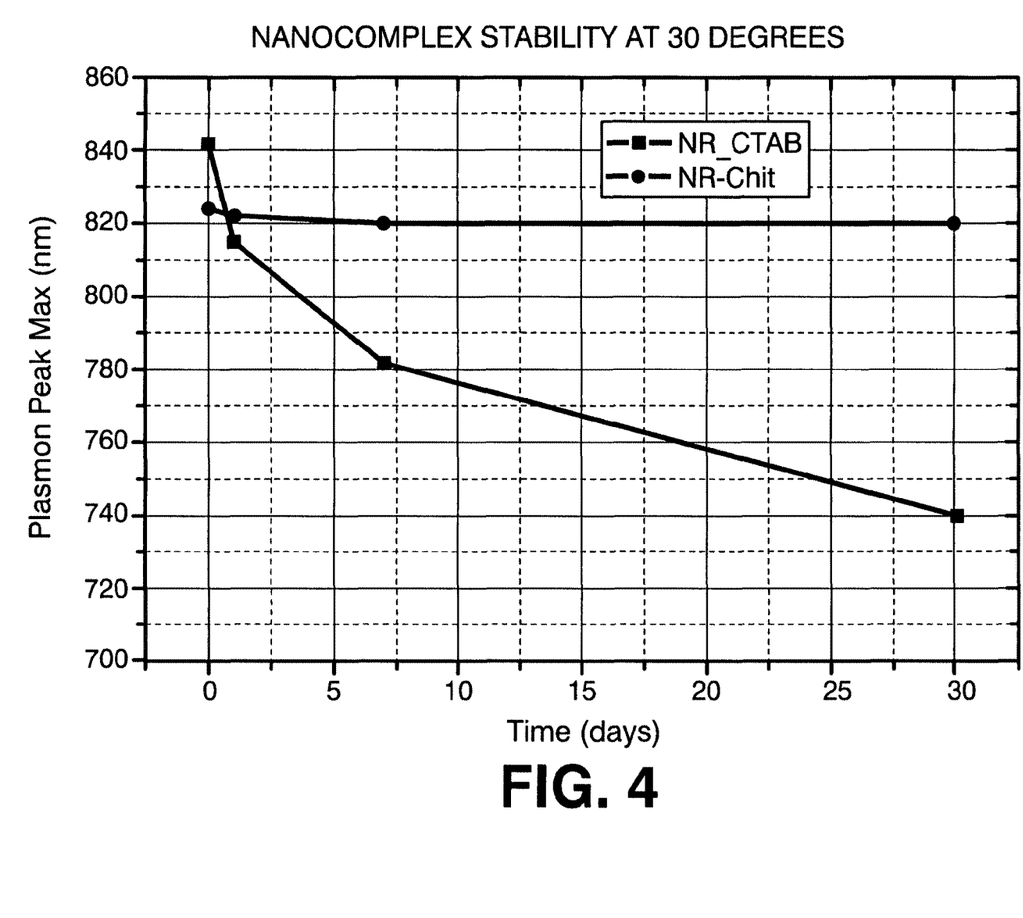
FIG. 4: Stability comparison of gold NR-Chit and as synthesized gold NR in CTAB surfactant as a function of time at 30° C.

Also, in principle nanocomplexes present in the composition of the invention can present any polycationic polymer as coating, preferably cosmetically or pharmaceutically acceptable polymers. Polycationic polymers in general show an affinity for NP and give rise to the formation of multiple weak covalent and/or coordination bonds. Preferred polycationic polymers are biocompatible polymers such as chitosans and those typically used in hair care and conditioner products, including quaternary ammonium polymers such as the polyquaternium-n series polymers, polyallyl ammonium polymers and copolymers thereof with polyamines and polyglucosamines. The specific interaction of primary amines with NP surfaces is well documented and can be assimilated to a weak covalent bond. The inventors have discovered that polyamine containing polymers form very stable coating layers on the NP surface due to a multi-anchoring interaction which allow obtaining very stable polycationic nanocomplexes presenting a moderate cationic charge (which is a characteristic of the amino groups). In FIG. 4, for example the increased stability of gold NR coated with chitosan is shown in comparison with NR as obtained in CTAB. These polycationic nanocomplexes are specially suited for the present application, due to the fact that this moderate cationic charge ensures an effective interaction with the highly charged hair cuticle while showing less interaction with other tissues.

Figure 5:
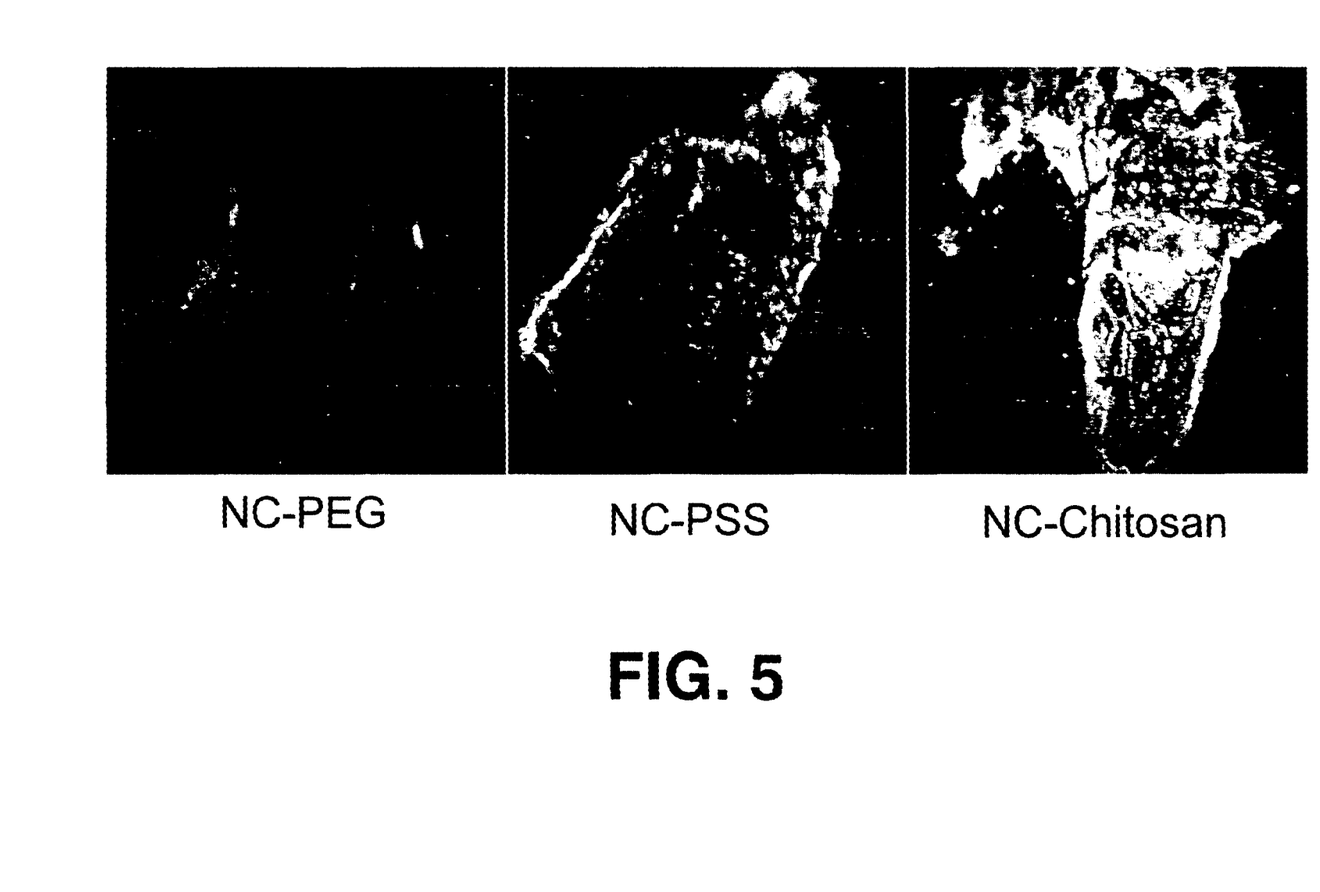
FIG. 5: Two-photon luminescence microscopy images showing the interaction of various coated nanocomplexes (Gold nanorods, GNR) with human hair cuticles: NC-PEG (nanocomplex with polyethylene glycol), NC-PSS (nanocomplex with polystyrene sulfonate) and NC-Chit (nanocomplex with chitosan).

In particular it has been shown that chitosan which is a biodegradable and biocompatible polymer, presents high interaction through its amine groups with the NP surface on one side, and with the negatively charged keratinized hair cuticle on the other side, ensuring good attachment of the nanocomplexes to the hair (see FIG. 5).

According thus to a preferred embodiment of the invention the composition of the invention comprises nanocomplexes wherein the chemical compound is a polycationic polymer, more preferably a polyamine containing polymer, and even more preferably chitosan.

Although the inventors of the present invention have shown that hair adhesion is more efficiently performed with polycationic nanocomplexes, due to the general negative charge of the hair cuticle, polyanionic nanocomplexes also show an effective interaction with hairs, essentially due to the presence of some positively charged points in the complex proteic biological structures of the hair. Thus according to a particular embodiment the composition of the invention comprises polycationic nanocomplexes.

The choice of using compositions comprising polycationic or polyanionic nanocomplexes, or mixtures thereof, can be influenced by aspects as formulation needs or economic issues.

According to a particular embodiments the NP forming the nanocomplex is constituted by any material capable of supporting Localized Surface Plasmon (LSP) resonances. LSP resonances are associated to an enhancement of both scattering and absorption of the light impinging on the particle. The enhanced absorption is responsible for the NP to efficiently heat-up. The localized heat generated by the nanocomplex, in contact with the hair, is thus directly transferred to it, damaging it and/or leading to temporal or permanent damage to the basal cells responsible for the regeneration process. In principle any material capable of supporting LSP resonance can be used for putting the present invention into practice. Examples of materials capable of sustaining LSP resonances and thus useful are metals and semiconductors. According to a particular embodiment the NP are of metal. Examples of metals are gold, silver, copper, aluminium etc. and any mixture thereof. In a preferred embodiment the NP is of gold.

According to another embodiment the NP forming the nanocomplex is a nanoshell capable of supporting a LSP resonance. Said nanoshells are well known structures constituted by a core of a dielectric material and a thin metal layer coated thereon. A typical dielectric material is for example silica but may be any other one, and the thin metal layer is constituted by any of the metals as defined above, preferably gold.

The nanocomplexes of the present invention are designed to present a LSP resonance maximum contained between 650-1200 nm, which is the window where the absorption and thus the photoheating of the biological tissues is minimal. In this way, the contrast of absorption between nanocomplexes and the surrounding tissues is maximized and the possible photothermal damage caused to the surrounding tissues and/or glands is avoided. According to a preferred embodiment the nanocomplex presents a LSP resonance maximum between 700 and 900 nm.

Figure 2:
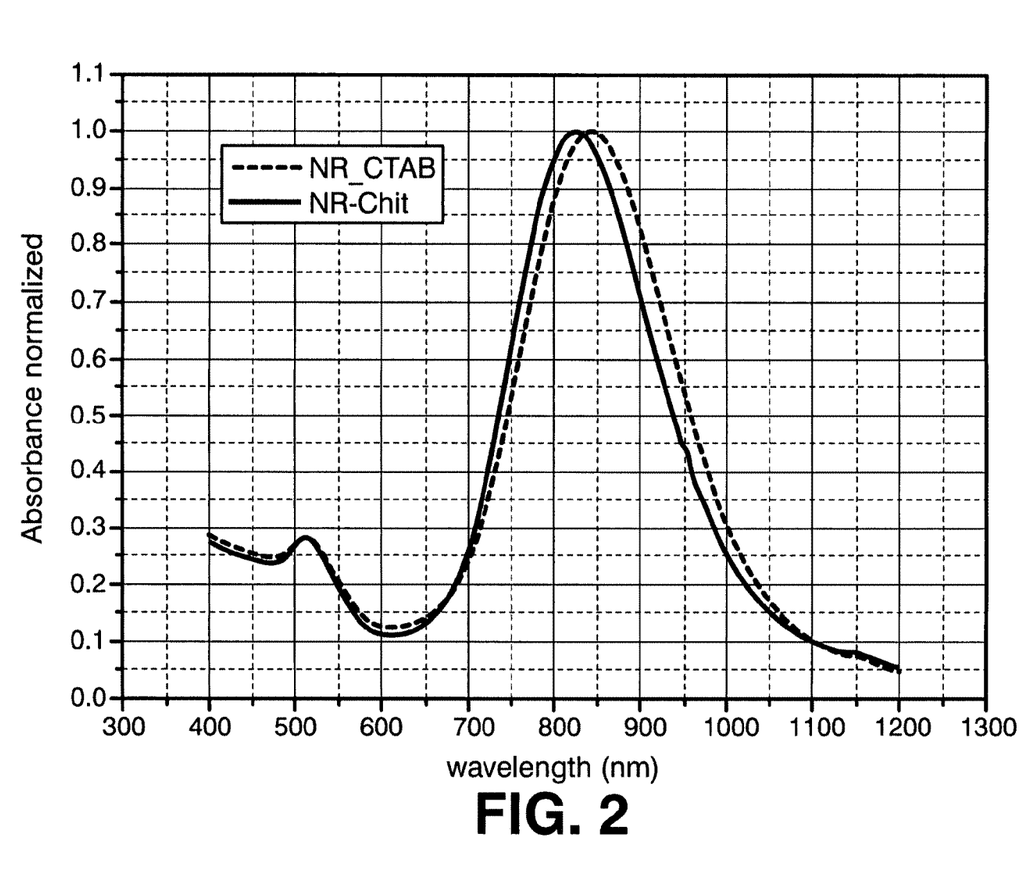
FIG. 2: Represents a comparison of the spectrum of gold nanorods in presence of the surfactant hexadecylcetyltrimethylammonium bromide (CTAB) (NR_CTAB) and after exchanging CTAB with chitosan (NR-Chit).

The nanocomplexes can be easily designed by the skilled person in the art to present a LSP resonance as required by the present invention. The skilled person in the art can, on one hand, easily obtain according to well known methods in the art, NP showing a determined resonance maximum, for instance within the window between about 650-1200 nm. On the other hand, it is also a well-known fact, which the skilled person takes into account when designing nanocomplexes to be used in the present invention that the preparation of nanocomplexes by way of coating nanoparticles with chemical compounds in general may lead to a modification of the LSP resonance maximums of typically 10 nm to 20 nm. This slight variation is of minor influence on the resonance of the resulting nanocomplex, since 10-20 nm is a much smaller range than the bandwidth of the LSP resonance, which is typically of the order of 100 nm. This small variation is illustrated in FIG. 2 where the particular case of the spectrum of gold nanorods before coating (as a suspension in the presence of its original surfactant CTAB) and after the CTAB bilayer has been exchanged with Chitosan.

The NP of the resonant nanocomplex can have in principle any form and size, as long as its LSP resonance is such that after its coating with a selected chemical compound the resulting nanocomplex presents a LSP resonance maximum between 650-1200 nm and more preferably between 700 and 900 nm.

In this respect it is also well known that the geometry of NP has influence on its resonance and heating ability. According to a preferred embodiment the NP are gold nanorods, since gold elongated NP of this kind, generate more heat than for instance gold nanospheres of the same volume (G. Baffou, R. Quidant, C. Girard. Heat generation in plasmonic nanostructures: Influence of morphology Appl. Phys. Lett. 2009, 94, 153109). This property is of interest according to the present invention, since the aim is to damage the hairs by heating, and more heat causes obviously more damage to them. Gold nanorods (GNR) useful for putting in practice the present invention can be easily obtained according to well known methods in the art.

Figure 3:
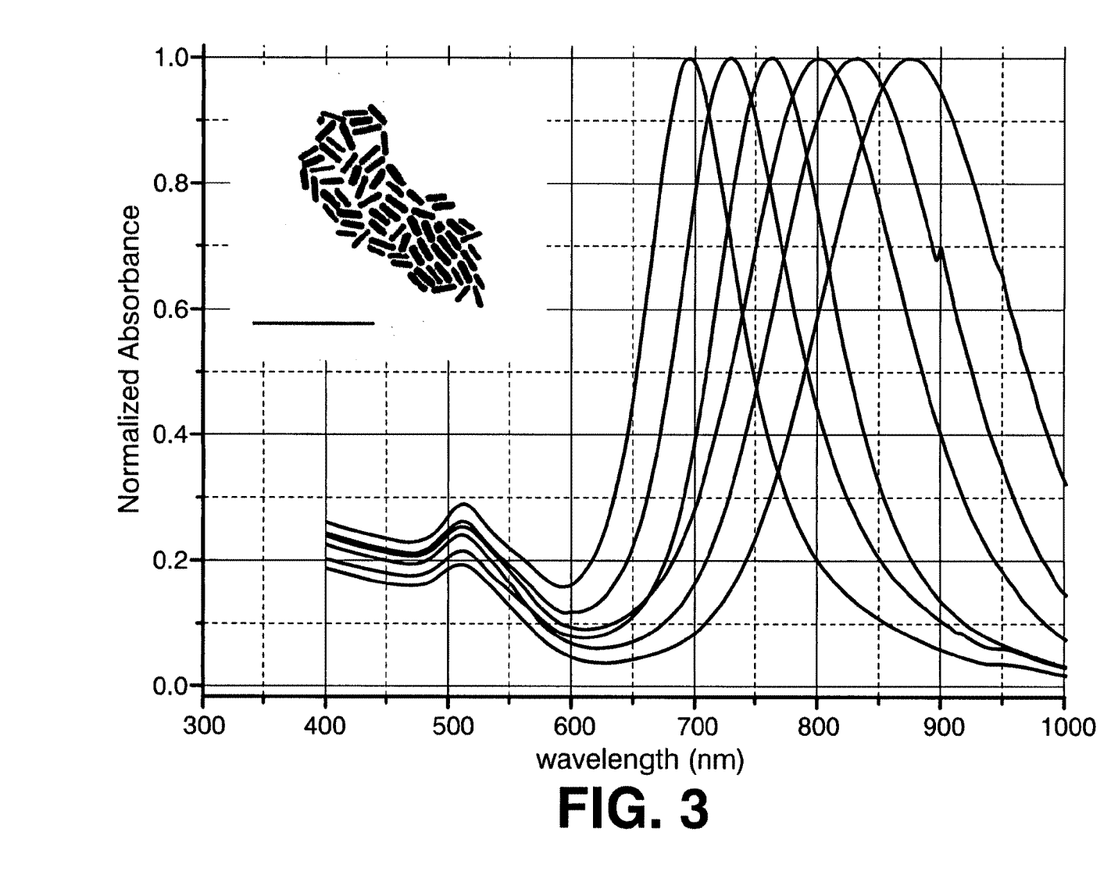
FIG. 3: Absorption spectra of gold nanorods of various aspect ratios leading to LSP resonance maximums ranging from 700-900 nm (see Example 1 for details). The transmission electron microscopy (TEM) image represents nanorods (NR) having an LSP resonance maximum around 820 nm.

According to a particular embodiment, GNR are prepared by the well known seed-mediated wet chemistry technique (Nikoobakht, B., El-Sayed, M. A. Preparation and Growth Mechanism of Gold Nanorods Using Seed-Mediated Growth Method. Chem. Mater. 2003, 15, 1957-1962) which renders maximally homogeneous size populations. The aspect ratio of the GNR achieved by this technique can be easily and carefully tuned by the skilled person so that resulting GNR present the desired LSP resonance maximum between about 650-1200 nm and more preferably between about 700-900 nm. Example 1 illustrates the seed-mediated wet-chemistry technique which provides GNR in an aqueous suspension in the presence of the surfactant, hexadecylcetyl-trimethylammonium bromide (CTAB). FIG. 3 shows various GNR spectra tuned between 700-900 nm by varying the aspect ratio of the GNR. As reference, a transmission electron microscopy (TEM) image is shown representing the aspect of the GNR presenting a LSP resonance maximum of around 820 nm.

According to another embodiment of the invention GNR, and in general any NP, with LSP resonance maximum at wavelengths higher than 800 nm can be selected when dark skin (featuring high concentration of melanin) is to be treated with the composition of the invention to avoid the absorption of light by melanin in the skin (absorption by melanin strongly decrease at wavelengths larger than 800 nm).

In a particular embodiment of the invention an aqueous suspension of GNR in the presence of CTAB surfactant, is first synthesised. Nanocomplexes are then prepared by exchanging the labile surfactant bilayer of the GNR with polyionic polymers, either polycationic or polyanionic. This is done by decreasing the surfactant concentration below the critical micelle concentration of 10 mM by repeated centrifugation and re-dispersion cycles and incubating the resulting suspension with a solution of the selected polymer, as illustrated in Example 2 for chitosan.

The stability of the resulting nanocomplexes is determined in different formulation mediums and monitored by their characteristic LSP resonance spectrum over time (periodic plasmon checks). An example of this can be seen in Example 3 and FIG. 4. The overall nanocomplex dimensions are determined by TEM measurements. For instance, a nanocomplex featuring a central resonance at 820 nm is ca. 12×50 nm.

Nanocomplexes present in the composition of the invention can present a surface assembled monolayer (SAM) as coating, preferably a cosmetically or pharmaceutically acceptable one. Said nanocomplexes can be readily obtained by well known processes comprising the exchange of surfactant ligands on NP with a heterobifunctional compound of the surface assembled monolayer type to obtain SAM-coated NP. As used in the present invention a heterobifunctional compound of the surface assembled monolayer type refers to a molecule which comprises at least a thiol group on one extremity of the molecule and at least another different functional negatively or positively charged group on the molecule, wherein said groups are situated so that the thiol group specifically bonds to the NP surface and the other functional negatively or positively charged group is able to rest on the outer surface of the coating of the nanocomplex so that it can strongly bind to the hair. In principle the rest of the structure of the heterobifunctional compound of the surface assembled monolayer type has no limitation and may present any possible structure. Examples of negatively or positively charged functional groups are carboxylates, sulfonates, secondary or tertiary amine groups and quaternary ammonium salts. A protocol for preparation of said nanocomplexes is illustrated in Example 4.

Examples of these heterobifunctional compounds of the surface assembled monolayer type present the following general formula:

$$HS-(CH_2)_n-X$$

wherein X represents a —COOH, —SO$_3$H, —N(CH$_3$)$_2$, or —N(CH$_3$)$_3{}^+$Cl and n is comprised between 2-22, preferably between 10-18

Other examples which are similar to those above but include and ethylene glycol repeating unit are compounds presenting the following formula:

$$HS-(CH_2)_n-(CH_2-CH_2-O)_m-X$$

wherein X represents a —COOH, —SO$_3$H, —N(CH$_3$)$_2$, or —N(CH$_3$)$_3{}^+$Cl and n is comprised between 2-22, preferably 10-18 and m is between 3-200.

Briefly, in a particular embodiment a heterobifunctional compound of the surface assembled monolayer type is added to an aqueous dispersion of gold nanorods under adequate conditions of ultrasounds and elevated temperature. After a defined period under these conditions the mixture is incubated at 30° C. until the reaction is completed (see Example 4). Preferably the amount of surfactant present in the aqueous solution is below the critical micelle concentration of surfactant of 10 mM.

The composition for topical application for photoepilation of the present invention comprises one or more of the nanocomplexes as above defined. The composition is cosmetically or pharmaceutically acceptable. According to a particular embodiment the composition is an aqueous suspension. The composition may however be also in form of a gel, milk, lotion, ointment or cream. The nanocomplexes concentration may vary within a wide range depending largely on the area exposed and the number of hairs per that area. According to a particular embodiment nanocomplexes are present in a cosmetically efficient amount. Under cosmetically efficient amount is to be understood the minimum amount to achieve a photoepilation effect in a photoepilation method. The composition may further contain other cosmetically or pharmaceutically acceptable ingredients such as solvents or cosmetic additives or vehicles.

In another aspect the invention relates to a new photoepilation method which comprises the steps of (i) applying to the skin surface the composition for topical application of the present invention, and (ii) applying a radiation to said surface of the skin.

The application of the composition described in step (i) may be carried out by simple deposition followed by a massage on the skin surface to be treated. The amount needed in each case can be readily determined by the skilled person.

The radiation used in step (ii) can be from any light source whose emission presents a spectral overlap with the LSP resonance of the nanocomplex comprised in said composition. Examples of light sources are those conventionally used in photoepilation methods, such as Intense Pulsed Light (IPL) or continuous wave and pulsed laser light.

According to a particular embodiment the light source is an IPL with a light delivered through a head piece window defining a set area of illumination (emitting between 600-900 nm). In this case, according to another particular embodiment a higher absorption contrast is achieved by filtering out the emission that does not overlap with the plasmon resonance, minimizing melanin absorption and thus tissue heating without contributing to hair damage.

The photoepilation method of the invention presents several advantages: increases the hair-skin absorption contrast, and consequently achieves improved efficiency compared with conventional methods, even at reduced radiation intensity. In addition the method presents improved universal applicability, e.g. application to dark as well as to fair hairs (white, blond and auburn) which represents an important advantage of the present method. Furthermore, the method decreases local injuries and side effects on the surrounding tissues and glands of the skin by substantially reducing the required light intensity to achieve a desired result.

In still a further aspect the invention relates to the use of nanocomplexes as defined above in a photoepilation method.

The foregoing is illustrative of the present invention. This invention however is not limited to the following precise embodiments described herein, but encompasses all equivalent modifications within the scope of the claims which follow.

EXAMPLES

Example 1

Synthesis of Gold Nanorods

Nanorods presenting LSP resonance maxima between 700-900 nm can be obtained by a 2-step, seed mediated process, by varying the silver nitrate (AgNO$_3$)/ascorbic acid/seed ratios (see FIG. 3).

Preparation of the Seed:

Colloidal gold seeds were first prepared by mixing aqueous solutions of hexadecylcetyltrimethylammonium bromide (CTAB, 0.2 M, 5 mL) and hydrogen tetrachloroaurate (III) hydrate (0.5 mM, 5 mL) both kept at 27° C. A freshly prepared aqueous solution of sodium borohydride (NaBH$_4$, 0.01 M, 0.6 mL) was then added, previously cooled to 4° C., under vigorous stirring for 2 minutes. At this point the seed was allowed to settle for 2 hrs at 30° C. to allow remaining NaBH$_4$ to evolve. This yielded a gold nanoparticle suspension of sizes between 1-2 nm, which were used as seed for the preparation of nanorods. This solution will be further referred as Seed Suspension.

Nanorod Growth:

The "growth solution" was now prepared and consisted of CTAB (0.2 M, 20 mL), to which varying amounts of silver nitrate stock (4 mM) was added depending on desired nanorod aspect ratio and allowed to mix under mild stirring. Hydrogen tetrachloroaurate(III) hydrate (1 mM, 20 mL) was added and gave rise to a yellow/brown solution. Once ascorbic acid (79 mM, 0.29 mL) was added the yellow/brownish solution, the mixture should turn colourless. Next, 72 L of aged Seed Suspension was added to the growth solution, mixed briefly and left undisturbed for 8 hrs at 30° C. to prevent CTAB crystallization. Initial colour change of the mixture should be noted after ca. 10 min. This procedure yielded a nanorod suspension presenting an LSP resonance maximum at around 820 nm (±20 nm) and a maximum absorption of 1.6 AU.

Example 2

Preparation of Chitosan Nanocomplexes with Gold Nanorods 20 ml of the GNR suspension obtained in Example 1 were centrifuged twice at 14000 rpm, 30 minutes. Each time the supernatant was removed and replaced by a 4 mM CTAB in water solution. To the resulting GNR suspension (20 ml), 4 ml of a chitosan solution (10 mg/ml, Mw: 5000) were added and placed in an ultrasound bath at 45° C. The resulting mixture was sonicated during 2 minutes and then placed at 30° C. overnight. The resulting chitosan nanocomplex was then centrifuged (14000 rpm, 30 minutes), the supernatant eliminated and finally redispersed with pure water to yield an absorption of around 2.5 AU at the LSP resonance maximum. The resulting aqueous suspension was directly used as further described for skin treatment.

Example 3

Stability of Chitosan Nanocomplex Compared to Nanorods in CTAB

An aqueous suspension of GNR in 100 mM CTAB (as synthesised) from Example 1 was compared to an aqueous suspension of the corresponding chitosan nanocomplex obtained as described in Example 2. Both suspensions are adjusted to an absorbance at the LSP resonance maximum of 1.5 AU and placed in an oven at 30° C. Samples are intermittently removed and measured by UV-vis spectroscopy and the stability is determined by the position of the LSPR maximum. Changes in this position indicate morphological modifications of the GNR and stability of the suspension. The obtained result (FIG. 4) indicates clearly an improved stability for the chitosan nanocomplex.

Example 4

Preparation of Cationic SAM Nanocomplex with Gold Nanorods 20 ml of the as synthesised GNR suspension was centrifuged twice at 14000 rpm, 30 minutes. Each time the supernatant was removed and replaced by a 4 mM CTAB in water solution. To the resulting GNR suspension (20 ml), 4 ml of an 11-mercaptoundecyltrimethylammonium bromide solution (10 mg/ml) was added and placed in an ultrasound bath at 45° C. This mixture was sonicated during 2 minutes and then placed at 30° C. overnight. After this time SAM nanocomplex was centrifuged (14000 rpm, 30 minutes), the supernatant eliminated and finally redispersed with pure water to yield absorption of around 2.5 AU at the LSP resonance maximum.

Example 5

Comparative Study of Nanocomplex Association to Hair

For this study three different nanocomplexes were prepared, varying in the final overall surface charge.
1) GNR coated with polyethylene glycol (NC-PEG), their surface potential being neutral. They were prepared by grafting HS-PEG-OCH$_3$ (Mw 5000) to the nanorod surface.
2) GNR coated with polystyrene sulfonate (NC-PSS, Mw 48000), their surface potential being anionic (obtained by the same method as described in Example 2)
3) GNR coated with chitosan (NC-Chit, Mw 5000), their surface potential being mildly cationic (obtained as in Example 2).

Preliminary experiments were performed with isolated human hairs from healthy volunteers. Hairs were incubated 30 minutes at 37° C. in aqueous solutions of the three different nanocomplexes and then washed with water. The interaction of the three different nanocomplexes with the hair surface was then studied. The observation of their distribution on human hairs is based on the ability of GNR to emit fluorescence upon absorption of two photons whose wavelength overlaps with the LSP resonance. This work was performed on a Nikon Eclipse Ti confocal microscope equipped with tunable laser source Mira 900F (Coherent Ltd). The laser was tuned at 810 nm and the power used was 40 milliwatts.

The brightness of the observed signals is directly proportional to the amount of nanocomplex attached to the hair. The obtained results show a charge-dependent adhesion of the three different nanocomplexes with the hair cuticle (see FIG. 5). The NC-PEG nanocomplex showed little adhesion to the hair, while the charged species NC-PSS and NC-Chit clearly showed increased accumulation. The anionic sample NC-PSS showed a good interaction, but clearly the best coverage of the hair was obtained with the NC-Chit nanocomplex.

Example 6

Application of Chitosan Nanocomplex to Pork Skin

Pork skin samples with dark hairs were obtained from the chest or the back of around 6 month aged pork. Samples of around 30 cm$^2$ were prepared by elimination of the excess of adipose tissue, cutting the excessive length of hairs down to around 1 mm length above the skin surface, followed by gentle washing of the skin with water and commercial detergents. The skin samples were then left to equilibrate at 37° C. in an incubator (95% humidity, 5% CO$_2$) during 40 minutes. The samples were then treated with an aqueous suspension of NC-Chit obtained following the procedure described in Example 2 having an absorption maximum around 800±20 nm and concentrated to obtain a maximum in absorption of around 2.5-3.0 AU. The quantity of nanocomplex suspension applied was 100 µl/cm$^2$. The nanocomplex suspension was applied with a gentle massage during 2 min using a planetary movement massage device (Relax and Tone). The skin samples were then left in the incubator at 37° C. for another 30 minutes before the IPL treatment (outlined in Example 7).

Example 7

Comparative Study of IPL Exposure of Pork Skin Samples Treated and not Treated with NC-Chitosan Nanocomplex Pork skin samples with dark hairs were obtained as described in Example 6 and left to stabilize at 37° C. in an incubator (95% humidity, 5% CO$_2$) during 30 minutes. A set of untreated samples (without any NC-Chit applied) followed exactly the same process of washing and incubation to be used as blanks on ILP treatment. The skin samples were then cut in slides of 1.5 cm×5 cm prior to being exposed with a commercial IPL source at different intensities (Ellipse Light Model STP with a HR3 applicator, wavelength range 600-900 nm).

The IPL treatment was performed on the samples using a single 30 millisecond pulse at different energies of 0, 9, 12 and 16 joules/cm². For reference the typical energy used in photoepilation treatments is around 16 j/cm². To perform the IPL treatment, the samples (with NC-Chit treated and not treated) were taken from the incubator, treated with a commercial optical gel for photoepilation and received the IPL pulse immediately after in order to keep the skin temperature as close as possible to 37° C. After IPL exposure the samples were left 30 minutes in the incubator at 37° C. and then a selected piece of 1 cm×1 cm was cut at the centre of the IPL impulse to be prepared for microscopy studies.

TABLE 1

Sample nomenclature

| Sample | Hair Color | Nanocomplex | IPL (j/cm2) |
|---|---|---|---|
| NT-0-BRW | Brown | No | 0 |
| NT-9-BRW | Brown | No | 9 |
| NT-12-BRW | Brown | No | 12 |
| NT-16-BRW | Brown | No | 16 |
| NC-0-BRW | Brown | Yes | 0 |
| NC-9-BRW | Brown | Yes | 9 |
| NC-12-BRW | Brown | Yes | 12 |
| NC-16-BRW | Brown | Yes | 16 |

Example 8

Sample Preparation for Microscopy Studies

The samples of 1 cm×1 cm obtained in the precedent example were incubated 16 h in a phosphate buffered saline (PBS)/4% formaldehyde solution. The samples were then washed twice (20 min) with pure water and step dried with ethanol (30% 8 hours, 70% 1 hour, 90% 1 hour, 100% 1 hour). For samples that needed longer storage time, the drying procedure was stopped at 70% of ethanol. The samples were then treated twice with p-xylene (20 min) and then included in paraffin blocks at 60° C. Paraffin blocks were prepared using Kunz CP-4 and WD-4 instruments. The blocks of paraffin including the sample was then cut in 20 µm slides using a Rotary 3003 PFM microtome. The obtained tissue slides were then mounted on microscopy glass slides, de-paraffined in xylene and rehydrated progressively for eosin staining. Furthermore, the obtained slides were stained with eosin during 30 seconds using standard staining procedures for microscopy in a Shandon Varistain 24-4 instrument from Thermo Electron Corporation.

Example 9

Study of the Nanocomplex Distribution on the Skin by Two Photon Microscopy

The samples treated or not with nanocomplex but without any IPL treatment (NC-0-BRW and NT-0-BRW) were then observed with two photon microscopy in order to study the nanocomplex distribution inside the hair follicle. In this method the nanocomplex may be distinguished due to their ability to emit visible light when irradiated with a laser at 800 nm.

Figure 6A:
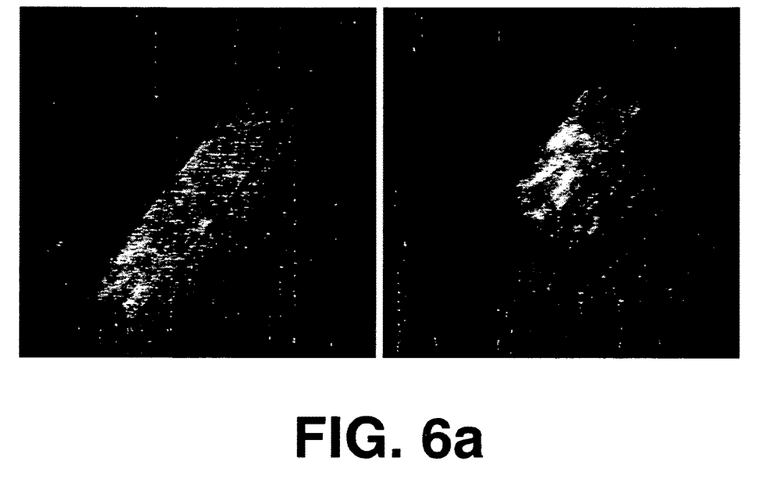
Figure 6B:
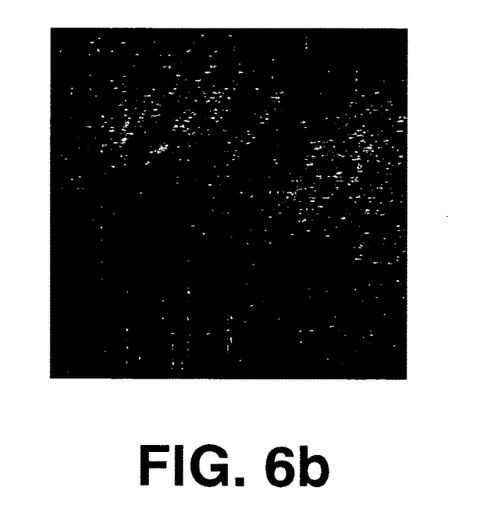
Figure 7:
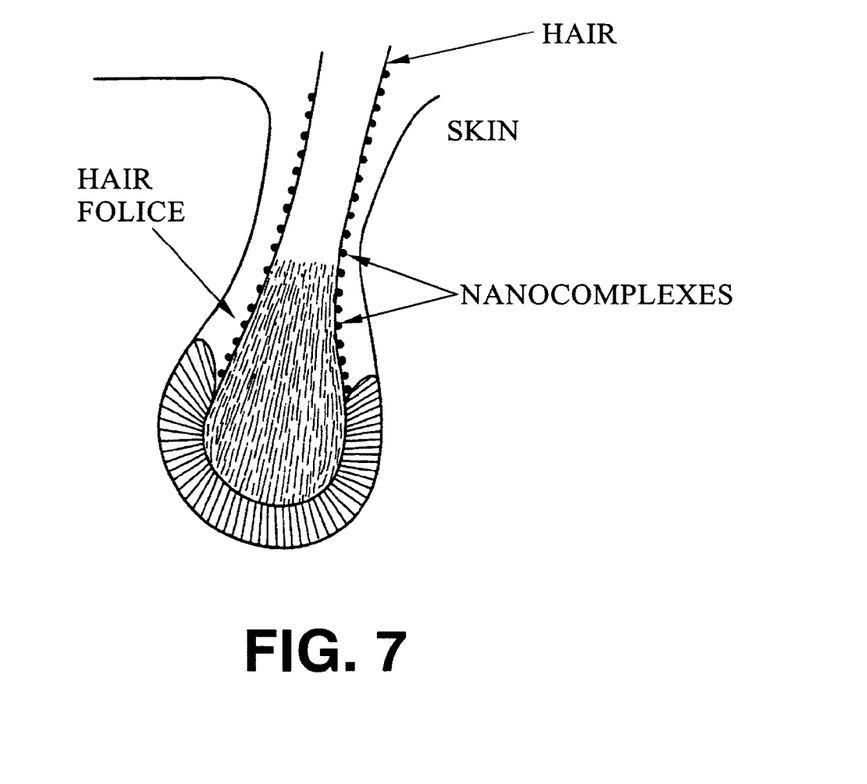
FIG. 7: Schematic representation of the interaction of nanocomplexes with the hair cuticle observed in FIG. 6.

The brightness of the signal obtained was, as in the Example 5, directly proportional to the amount of nanocomplex interacting with the hair cuticle. Images showed clear penetration of the nanocomplex into the hair follicle (at least 1 mm deep) and their accumulation at the hair cuticle level with little association to other tissues (FIG. 6a). For reference, an image of the untreated sample with nanocomplex (NT-0-BRW) skin sample was also taken showing the autofluorescence of hair and tissue under identical conditions (FIG. 6b). FIG. 7 shows schematically the expected interaction of the nanocomplex with the hair cuticle inside the hair follicle.

Example 10

Study of the IPL Exposure Effect on the Hair Root by Optic Microscopy

In order to monitor the actual damage to the hair follicle resulting from the IPL exposure all the samples prepared as described in Example 7 were observed by conventional bright field optical microscopy.

Figure 8A:
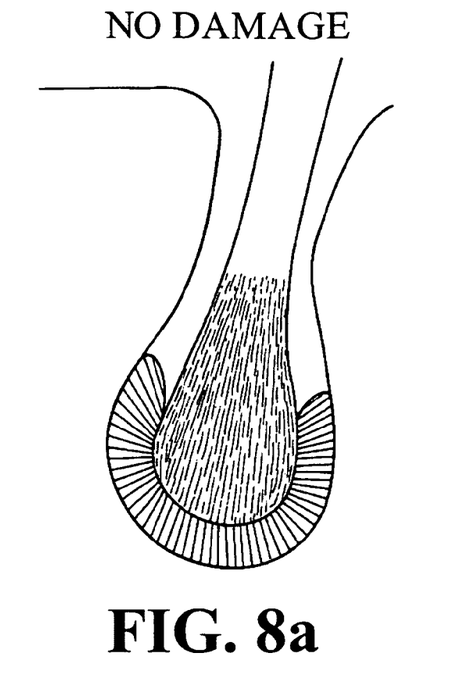
Figure 8B:
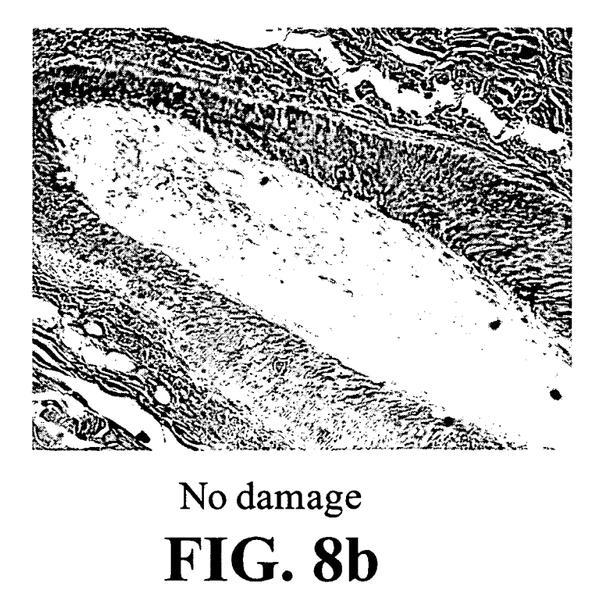
Figure 9A:
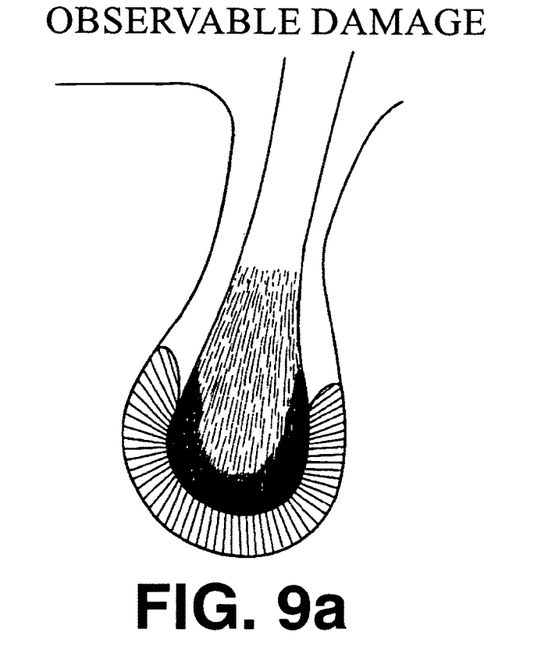
Figure 9B:
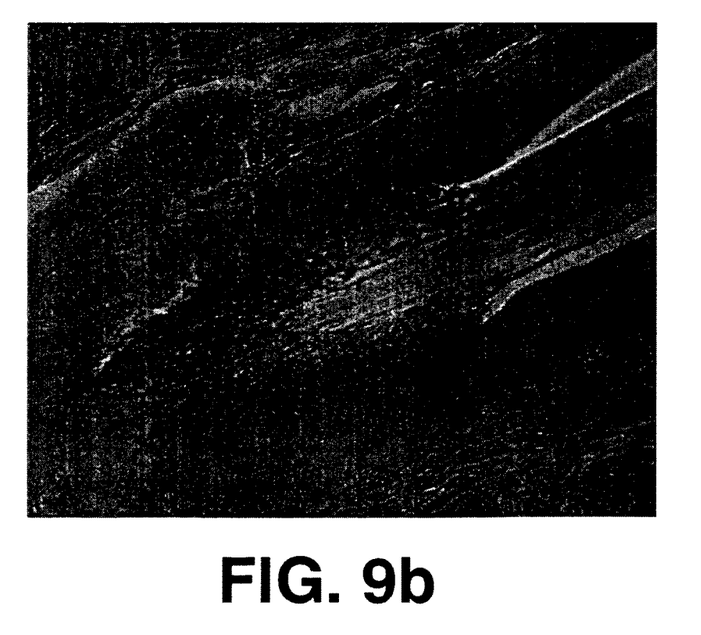
Figure 10A:
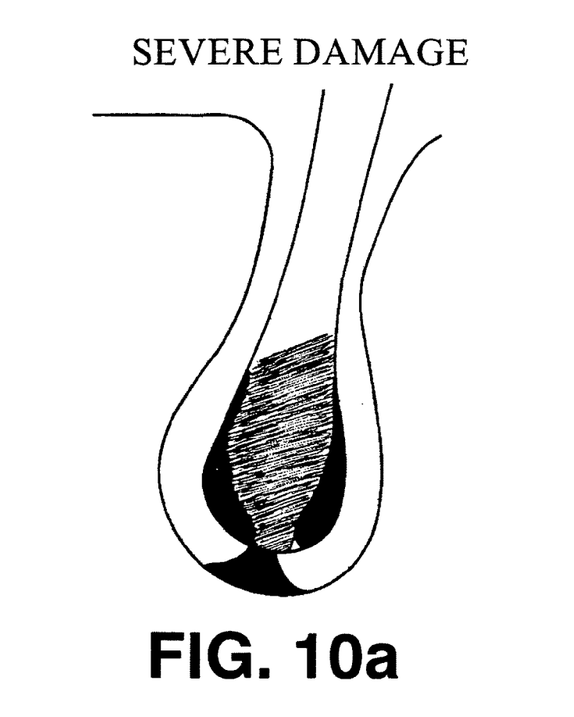
Figure 10B:
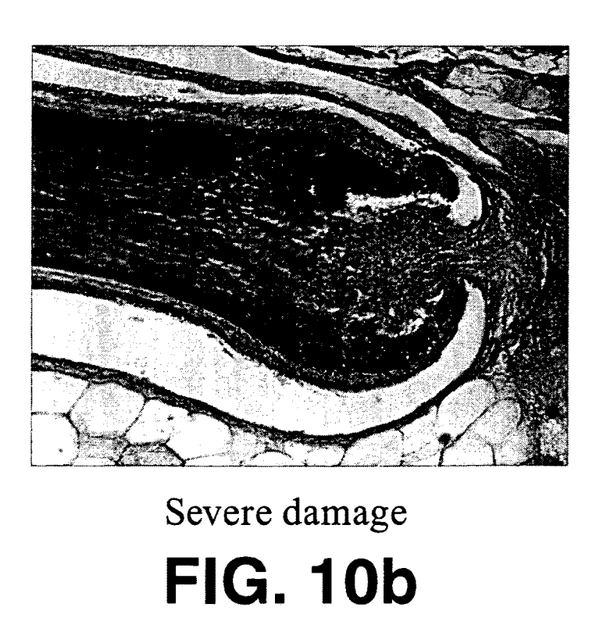

Results are presented in Table 2 and give the proportion of the different levels of damage as observed on a defined population of hairs. The data clearly show that, at a given exposure intensity, the samples treated with NC-Chit show much higher proportion of hairs with severe damage. Consequently, a majority of hairs with severe damage can be obtained with incident intensity significantly lower as compare to non-treated samples. The level of damage was classified from the observation of different hair micrographs. FIGS. 8-a, 9-a and 10-a show schematically the level of damage classification and corresponding FIGS. 8-b, 9-b and 10-b show real examples of the level of damage observed at the hair root level.

TABLE 2

Comparative table of the observed effects at the hair root level for the different IPL treatments in the case of brown hair. The % are not formally statistical but obtained from around 30 slides for each sample.

| | Damage | | |
|---|---|---|---|
| Sample | None | Observable | Severe |
| NT-0-BRW and NC-0-BRW | 100% | 0% | 0% |
| NT-9-BRW | 65% | 28% | 7% |
| NT-12-BRW | 18% | 59% | 23% |
| NT-16-BRW | 0% | 42% | 58% |
| NC-9-BRW | 25% | 22% | 53% |
| NC-12-BRW | 0% | 27% | 73% |
| NC-16-BRW | 0% | 20% | 80% |

Example 11

Study of the IPL Exposure Effect on the Hair Root of Fair Hairs by Optic Microscopy In order to demonstrate the applicability of the invention to other types of hairs independently of their melanin content, previous experiments were repeated on another set of pork skin samples showing a majority of fair hairs. The samples were prepared following exactly the same procedures used for brown hairs (see Examples 6 to 8). For reference, the samples treated with the nanocomplex composition (NC-X-F where X corresponds the IPL energy administered in Joule/cm² as described in Example 7) were compared to untreated samples (NT-X-F). The samples were then processed as described in Example 8 and monitored using bright field microscopy.

The obtained results are presented in Table 3. In this case the observed damage to the hair root was classified in only two categories: "severe damage" or "no damage". Unlike brown hairs, the lower contrast of fair hairs in bright field microscopy does not allow discriminating an intermediate regime of "observable damage". The data clearly show a clear improvement of the treatment on the hair damage efficiency.

TABLE 3

Comparative table of observed effect at the hair root level for different IPL treatments in the case of fair hair. The % are not formally statistical but obtained from around 20 slides for each sample.

| Sample | Damage | | |
|---|---|---|---|
|  | None | Observable | Severe |
| NT-0-F and NC-0-F | 100% | — | 0% |
| NT-9-F | 88% | — | 12% |
| NT-12-F | 57% | — | 43% |
| NT-16-F | 44% | — | 56% |
| NC-9-F | 58% | — | 42% |
| NC-12-F | 39% | — | 61% |
| NC-16-F | 19% | — | 81% |

The invention claimed is:

1. A composition for topical application on skin for photoepilation comprising nanocomplexes which comprise a nanoparticle of a material selected from the group consisting of metals, semiconductors and their mixtures supporting a Localized Surface Plasmon resonance which is coated by forming at least a bond, coordinative or covalent, with at least a polycationic polymer or a heterobifunctional compound of the surface assembled monolayer which comprises at least a thiol group on one extreme of the molecule and at least a positively charged functional group on the other extreme.

2. A composition according to claim 1, wherein the nanocomplex presents a localized surface plasmon resonance maximum between 650-1200 nm.

3. A composition according to claim 2, wherein said nanoparticle is of gold.

4. A composition according to claim 3, wherein said nanoparticle is a gold nanorod.

5. A composition according to claim 3, wherein the nanoparticle is a nanoshell.

6. A composition according to claim 2, wherein the nanoparticle is a nanoshell.

7. A composition according to claim 1, wherein said nanoparticle is of gold.

8. A composition according to claim 7, wherein said nanoparticle is a gold nanorod.

9. A composition according to claim 7, wherein the nanoparticle is a nanoshell.

10. A composition according to claim 1, wherein the nanoparticle is a nanoshell.

11. A composition according to claim 1, wherein the polycationic polymer is a polyamine containing polymer.

12. A composition according to claim 1 wherein the polycationic polymer is selected from the group consisting of: quaternary ammonium polymers, polyallyl amine polymers and copolymers thereof with polyamines and polyglucosamines.

13. A composition according to claim 11, wherein the polyamine containing polymer is chitosan.

14. A composition according to claim 1, wherein the heterobifunctional compound of the surface assembled monolayer type presenting the following general formula:

$HS-(CH_2)_n-X$ wherein X represents a $-N(CH_3)_3^+Cl$ and
n is comprised between 2-22, preferably between 10-18
or the following formula:

$HS-(CH_2)_n-(CH_2-CH_2-O)_m-X$ wherein X represents a $-N(CH_3)_3^+Cl$ and
n is comprised between 2-22, preferably 10-18 and m is between 3-200.

15. A composition according to claim 1 which is an aqueous suspension.

16. A photoepilation method which comprises the steps of (i) applying to a skin surface a composition according to claim 1, and (ii) applying a radiation of a light source having an emission that has a spectral overlap with the Localized Surface Plasmon resonance of the nanocomplex comprised in said composition to said surface of the skin.

17. A photoepilation method according to claim 16, wherein the nanocomplex presents a localized surface plasmon resonance maximum between 650-1200 nm.

18. A photoepilation method according to claim 16, wherein said nanoparticle is either a nanorod or a nanoshell.

19. A photoepilation method according to claim 16, wherein said polycationic polymer is a polyamine containing polymer.

20. A photoepilation method according to claim 16, wherein the polycationic polymer is selected from the group consisting of: quaternary ammonium polymers, polyallyl amine polymers and copolymers thereof with polyamines and polyglucosamines, and (ii) applying a radiation to said surface of the skin.

21. A photoepilation method according to claim 16, wherein the nanocomplex presents a localized surface plasmon resonance maximum between 700 and 900 nm.

22. A photoepilation method according to claim 16, wherein the light source is Intense Pulsed Light (IPL).

23. A photoepilation method according to claim 16, wherein the light source is a continuous wave or a pulsed laser light.

24. A composition according to claim 1, wherein the nanocomplex presents a localized surface plasmon resonance maximum between 700 and 900 nm.

* * * * *